United States Patent [19]

Goshgarian

[11] 4,392,826
[45] Jul. 12, 1983

[54] PALATAL ARCH BAR WITH COMBINATION LOCKING DEVICE AND ELASTIC ANCHOR

[76] Inventor: Robert A. Goshgarian, 2634 Grand Ave., Waukegan, Ill. 60085

[21] Appl. No.: 348,676

[22] Filed: Feb. 16, 1982

[51] Int. Cl.³ .............................................. A61C 7/00
[52] U.S. Cl. ........................................ 433/7; 433/17
[58] Field of Search ............................ 433/20, 17, 6, 7

[56] References Cited

U.S. PATENT DOCUMENTS 3,477,129  11/1969  Rubin .................................... 433/17
3,792,529  2/1974  Goshgarizu ............................. 433/6

*Primary Examiner*—Robert Peshock
*Attorney, Agent, or Firm*—Lloyd L. Zickert

[57] ABSTRACT

A removable orthodontic palatal arch bar for applying rotating, expanding, contracting, intruding and/or torqueing forces to a pair of opposed molars which includes an arch bar of round wire having doubled-over ends receivable by lingual tubes mounted on the molars and a combination locking device and elastic anchoring means extending from the doubled over ends along the gingival and distal sides of the tubes.

5 Claims, 4 Drawing Figures

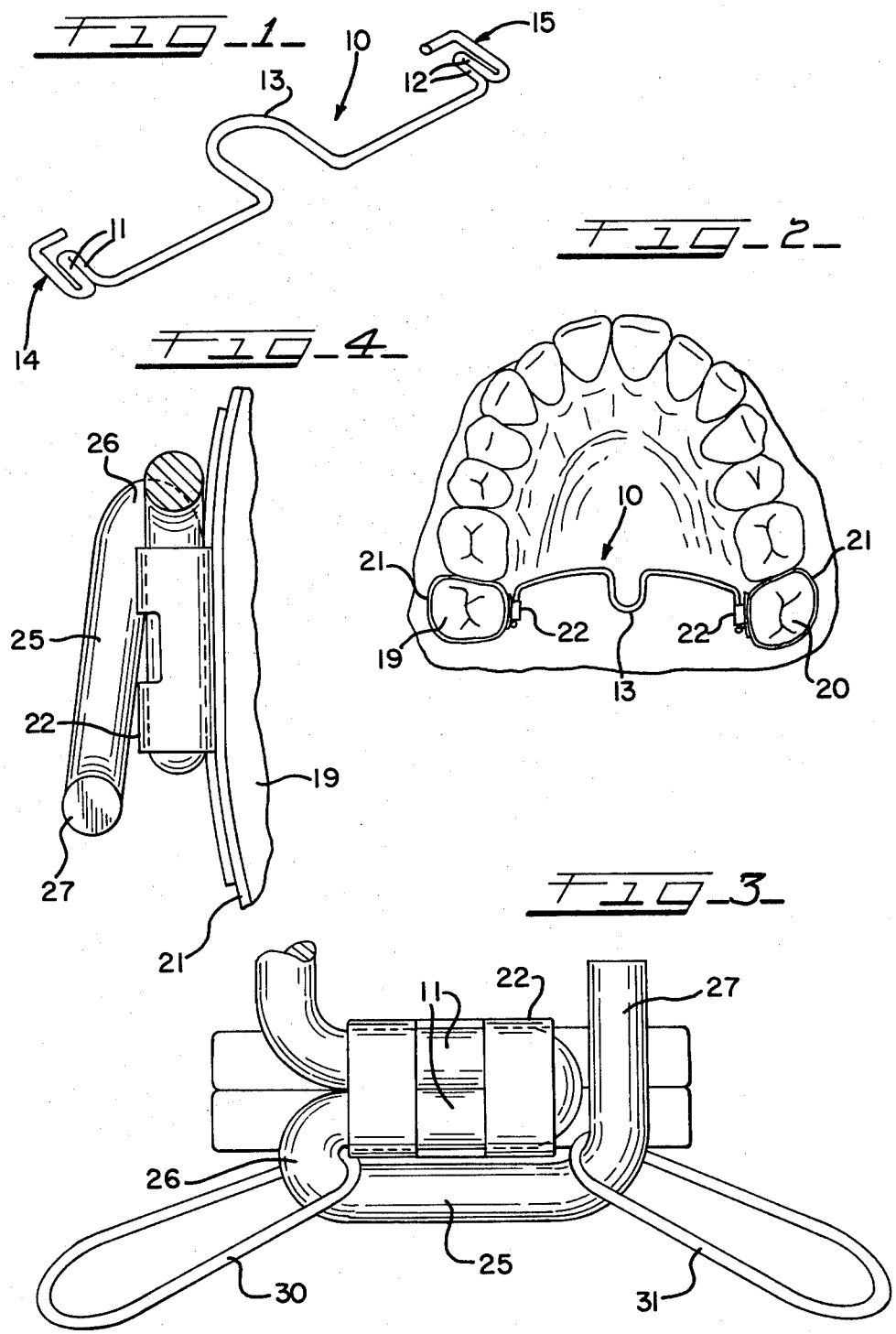

PALATAL ARCH BAR WITH COMBINATION LOCKING DEVICE AND ELASTIC ANCHOR

This invention relates in general to an orthodontic palatal arch bar to apply forces to the molars in the upper arch of a person, and more particularly to an arch bar for removable attachment to retention means on the molars and having means for locking the bar to the retention means and to receive elastics.

The present invention is an improvement over my palatal arch bar invention disclosed in U.S. Pat. No. 3,792,529. It has been found that occasionally the arch bar, when removably attached to lingual sheaths or tubes, may work loose, after which the patient may inadvertently swallow the arch bar. Further, the arch bar of the patent has been heretofore used only for applying forces to the first molars. It has not been a good practice to apply it to the second molars because of the added danger of swallowing the bar if it came loose. When applied to the first molars, it is subjected to continual tongue thrust which can result in loosening of the bar from the lingual tubes or sheaths. Moreover, it is often necessary to remove the bar and adjust it during treatment of a patient which may result in loosening the fit of the ends of the bar with respect to the sheaths or tubes. Accordingly, there has been a need to inhibit or prevent the loosening and accidental separation of the bar ends from the sheaths or tubes.

Heretofore, palatal arch bars have been locked to the lingual sheaths or tubes by ligating the bar to the tube. However, the sheath or tube used must include means for allowing the attachment of the ligating wire to the tube. It is well known that ligature wire ends can be a severe irritation to the patient as they define sharp edges against which the tissues may engage. It is also known that ligature wire sometimes comes loose and then the ligature wire may be accidentally swallowed by the patient and also allow the palatal arch bar to loosen and be accidentally swallowed by the patient. While the ligature wires and/or the arch bars usually pass through the body, there is a danger that they may not and also that they may be aspirated into the lungs, thereby causing serious injury to a patient. It is also known that to apply a ligature wire requires additional time of the orthodontist when mounting the palatal arch bar in place.

Another heretofore used locking system involves providing a latching indent on the lingual side of the lingual tube which is intended to latch the doubled-over end of the bar upon insertion. This has not been satisfactory, as latching does not always occur and unlatching can occur due to forces applied against the arch bar during patient use such as by tongue thrust.

The present invention overcomes the problems and difficulties heretofore encountered with the arch bar of the above patent in that it provides an arch bar having a simple locking device which may be easily operated to lock and unlock the ends of an arch bar to the sheaths or tubes where locking is positive and essentially failsafe. The locking device is in the form of a U-shaped locking bar which extends from each of the doubled over ends of the arch bar such that it is disposed along the gingival and distal of the sheath or tube in which the arch bar end is mounted, thereby securely and positively locking the arch bar end to the tube. When it is desired to remove the arch bar for adjustment, the locking device may simply be bent lingually so that removal can be accomplished. The U-shaped locking bar additionally defines arms or hooks which can receive an elastic for applying forces to other teeth, thereby broadening the use of the arch bar.

It is therefore an object of the present invention to provide an improved palatal arch bar capable of being selectively and positively locked in place on the teeth of the patient to prevent accidental separation from the teeth.

Another object of the present invention is in the provision of a new and improved palatal arch bar having a combination locking device and elastic anchor.

A still further object of the present invention is to provide an improved palatal arch bar having a locking device that may be easily operated for allowing the positive locking of an arch bar in place or the removal of an arch bar for adjustment or other purposes.

A still further object of the present invention is to provide an improved palatal arch bar having a locking device which can be easily manipulated to allow the arch bar to be positively locked or unlocked relative to the lingual tubes on which it is mounted and which eliminates the necessity of using ligature wire to lock an arch bar in place on the tubes, as well as eliminating the necessity to provide a special sheath or tube for receiving a ligature wire or a specially constructed tube having a latching indent, thereby making it safer to use palatal arch bars and also to reduce the time spent by the orthodontist in inserting and/or removing for adjustment such arch bars, and to further allow the placement on the second molars.

Other objects, features and advantages of the invention will be apparent from the following detailed disclosure, taken in conjunction with the accompanying sheets of drawings, wherein like reference numerals refer to like parts, in which:

FIG. 1 is an enlarged perspective view of the improved palatal arch bar of the present invention before it is activated;

FIG. 2 is an inferior plan view of an upper dental arch showing the palatal arch bar mounted in position on the patient's upper permanent second molars;

FIG. 3 is a greatly enlarged lingual side elevational view of the locking device in association with the doubled over end and lingual tube and taken substantially along line 3—3 of FIG. 2; and FIG. 4 is an occlusal plan view of the doubled over end of the arch bar in mounted relation with a lingual tube and illustrating the locking device in unlocked position to allow removal or insertion of the doubled over end of the bar with respect to the lingual tube.

Referring now to the drawings and particularly to FIG. 1, the improved palatal arch bar of the present invention, generally designated by the numeral 10, is shown in its form as received by the orthodontist and prior to being activated for a particular patient. Activation depends on the type of forces desired, and various forms of activation are well illustrated and described in my prior U.S. Pat. No. 3,792,529. The arch bar generally includes doubled-over ends 11 and 12, an intermediate U-shaped compression loop 13, and locking devices 14, 15 at the doubled over ends 11 and 12.

Heretofore, the palatal arch bar of the aforementioned patent has been constructed of 0.036 inch diameter stainless steel wire. While it can be appreciated that the arch bar of the present invention may be made of the same size of wire, it may also be understood that it can be made of wire of other types and other diameter sizes depending upon the desired use. However, it is contemplated that the improved arch wire of the present invention be made of 0.030 inch diameter wire so that it can easily be accommodated for mounting on the second upper molars. It is also possible that a patient could be treated by mounting one of the arch bars of the present invention on the second molars and another on the first molars whereby additional corrective forces can be applied to the teeth and which would reduce the time needed for treatment. Moreover, use of 0.030 wire will make it easier to manipulate the locking devices of the present invention on an arch bar. It should be further appreciated that the arch bar will be provided in a variety of lengths to fit dental arches of various dimensions, as discussed more thoroughly in my above patent.

As shown more clearly in FIG. 2, the palatal arch bar 10 is illustrated in mounted position on the patient's upper second permanent molars. The molars are identified by the numerals 19 and 20, each of which has a metal band 21 suitably adhesively secured thereto and on which is suitably secured a metal lingaul sheath or tube 22 of a type that is commercially available. The lingual tube would be sized to receive a doubled-over end of the palatal arch bar, and where the arch bar is 0.030 inch in diameter, the opening for the lingual tube would be about 0.060×0.030 so that the doubled-over end would be snugly or tightly received the tube. It will be appreciated that the lingual tube would be mounted on the band such as by welding or soldering and positioned so that the opening through the tube would extend substantially mesiodistally. In the event that the wire used to form the palatal arch bar is of a larger or smaller diameter, the opening for the lingual tube would similarly be larger or smaller to accommodate the size of wire for the arch bar.

Referring now particularly to FIGS. 3 and 4 which illustrate one end of the arch bar respectively in locked and unlocked position on a lingual tube, the locking device 14 is generally U-shaped and includes a central arm 25 which when in locked position lies in the plane of the lingual tube and at the gingival side thereof, a leg 26 connecting the central arm 25 to the doubled over ends 11, and an end leg 27 extending along the distal end of the lingual tube 22 when in locked position to prevent mesial movement of the doubled-over ends such that they can be separated from the lingual tube.

As seen particularly in FIG. 4, when it is desired to insert the doubled-over ends or remove them from the tube 22, the central arm and leg 27 are bent together lingually so that the end leg 27 is clear of the lingual tube 22, as illustrated. Thus, in operation it may readily be appreciated that the central arm and end leg 27 will be in the position 24 when the arch bar is being mounted on the lingual tubes whereby the doubled over ends are inserted mesially into the lingual tubes. After the ends are in seated position, as shown in FIG. 4, the central arm and end leg 27 are bent buccally until the central arm 25 lies gingivally in the same plane as the tube 22 and the end leg 27 is disposed also in the same plane as the tube and over the distal end of the tube, as shown in FIGS. 2 and 3, thereby locking the arch bar to the tube. Similarly, when removing the palatal arch bar, it is only necessary to bend out the end leg 27 and the central arm 25 to a position such as shown in FIG. 4.

From the foregoing, it can be appreciated that the locking device 14 eliminates the need for use of any ligatures to lock the doubled-over ends of the lingual tubes and it can be simply and easily manipulated by the orthodontist during the mounting or removing of the palatal arch bar. Moreover, the invention eliminates the need to use a lingual tube with a latching indent, which decreases the cost of the tube as it is simpler to manufacture.

The locking device 14 additionally permits the anchoring of elastics to the molar teeth on which the arch bar is mounted. As illustrated in FIG. 3, the locking device provides arms or hooks onto which an elastic 30 can be used in a Class I cuspid retraction and counter-rotation of cuspids and an elastic 31 for Class II cross elastics. A hook has been heretofore provided on a palatal arch bar which extends from the doubled over end to receive a cross elastic.

It therefore can be appreciated that the palatal arch bar of the present invention allows for the easy locking of a bar to molars and can easily be used for second molars without endangering the dislodging of the bar and subsequent accidental swallowing of same. Moreover, it enables the anchoring of elastics for applying forces to other teeth during orthodontic treatment.

It will be understood that modifications and variations may be effected without departing from the scope of the novel concepts of the present invention, but it is understood that this application is to be limited only by the scope of the appended claims.

The invention is hereby claimed as follows:

1. In an orthodontic appliance for applying rotating, expanding, contracting, intruding, and/or torquing forces to a pair of opposed molars in the upper arch of a person, wherein the appliance includes lingual tubes mounted lingually on said molars with mesiodistally extending openings therethrough, and a palatal arch bar having doubled-over ends received mesially by said lingual tubes, the improvement being in means for locking the arch bar to the lingual tubes, which locking means includes a U-shaped locking bar extending from each of the doubled-over ends and over the distal ends of the lingual tubes to prevent removal of said ends from the tubes.

2. The improvement defined in claim 1, wherein said U-shaped locking bar may be selectively bent between locking and unlocking positions.

3. The improvement defined in claim 2, wherein each said U-shaped locking bar includes an arm extending along the gingival side of the respective tube and in the same plane thereof when in locked position, and a leg extending along the distal side of the tube and in the same plane thereof when in locked position.

4. The improvement defined in claim 3, wherein said locking bar defines elastic anchors at the mesial and distal ends of said tubes.

5. An orthodontic appliance for applying rotating, expanding, contracting, intruding, and/or torquing forces to a pair of opposed molars in the upper arch of a person, wherein the appliance includes tubular means mounted on the lingual sides of said molars having a mesiodistally extending opening therethrough, a palatal arch bar of spring steel of a length substantially equal to the palatal distance between the tubular means and having terminal ends and an open U-shaped spring loop intermediate the terminal ends thereof, the terminal ends being received in the openings of the tubular means and having means coacting with the tubular means to preclude relative rotation therebetween, the improvement being in means locking the terminal ends of said palatal arch bar to said tubular means including locking bars integral with and extending from said terminal ends and selectively movable into and out of locking position over the ends of the openings in said tubular means opposite to the ends thereof into which the terminal ends of said arch bar are inserted to selectively lock the arch bar to the molars.

* * * * *